US005741491A

United States Patent [19]
Jones

[11] Patent Number: 5,741,491
[45] Date of Patent: Apr. 21, 1998

[54] MEDICINAL COMPOSITION FOR DIABETES

[75] Inventor: Sherman Jones, Darewell, Canada

[73] Assignee: Isotechnika Incorporated, Edmonton, Canada

[21] Appl. No.: 524,432

[22] Filed: Sep. 6, 1995

[51] Int. Cl.$^6$ ............................................. A61K 35/78
[52] U.S. Cl. ............................................. 424/195.1; 514/866
[58] Field of Search ..................... 424/195.1; 514/866

[56] References Cited

U.S. PATENT DOCUMENTS

| | | | |
|---|---|---|---|
| 685,853 | 11/1901 | Joie | 426/596 |
| 1,520,122 | 12/1924 | Gephart et al. | 426/597 |
| 2,971,844 | 2/1961 | Bosanac | 429/195.1 |
| 3,080,237 | 3/1963 | Bonotto | 426/319 |
| 3,113,028 | 12/1963 | Cooper et al. | 426/330.3 |
| 3,928,584 | 12/1975 | Hudson | 424/195.1 |
| 3,932,628 | 1/1976 | Hudson | 424/195.1 |
| 4,357,361 | 11/1982 | Lunder et al. | 426/597 |
| 4,469,685 | 9/1984 | Kojima et al. | 424/195.1 |

FOREIGN PATENT DOCUMENTS 0 030 444   6/1981   European Pat. Off. .

OTHER PUBLICATIONS

Gabriel Garnier et al.: "Ressources Medicinales de la Flore Francaise" 1961, Vigot Freres Editeurs, Paris XP002021703 see p. 294–p. 297.

*Primary Examiner*—John W. Rollins
*Attorney, Agent, or Firm*—Beveridge, DeGrandi, Weilacher & Young, LLP

[57] ABSTRACT

The invention is a method and composition for treating diabetes using an extract derived from *Heracleum lanatum* and a species of Populus.

19 Claims, 2 Drawing Sheets

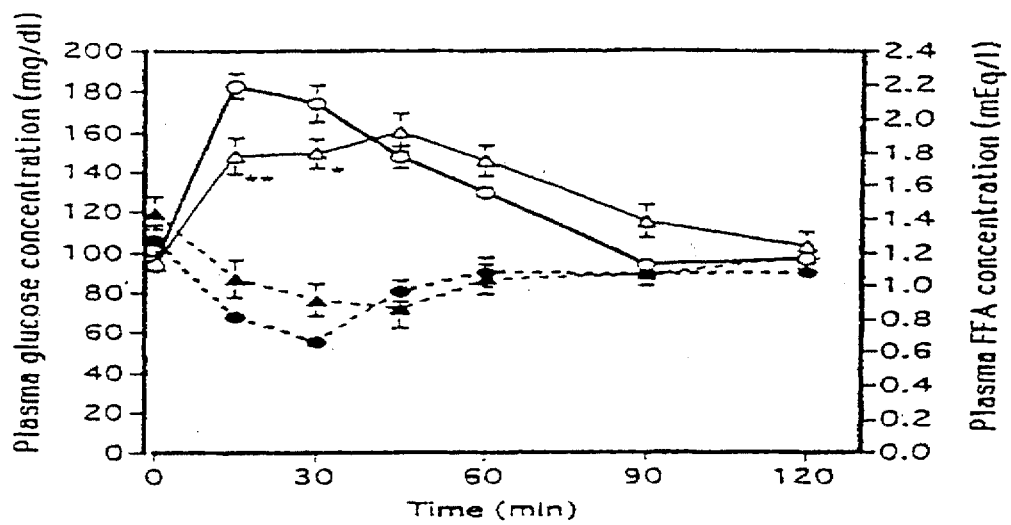
Effects of herb mix extract on plasma glucose and FFA (Free Fatty Acid) concentration in glucose-loaded rats in experiment 1. Each point represents the mean ± S.E.
Legend: -O-; Glucose levels of control rats receiving no herb mix, -△-; Glucose levels of rats treated with herb mix, -●-;, -▲-;, *: $p<0.05$, **: $p<0.01$.

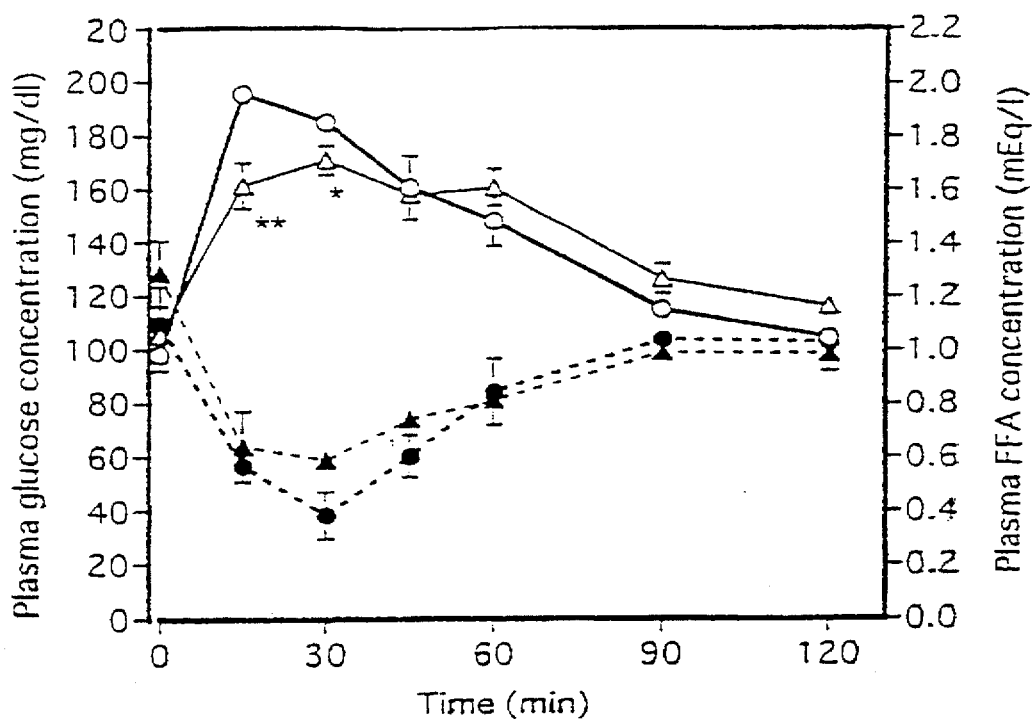
Effects of herb mix extract on plasma glucose and FFA (Free Fatty Acid) concentration in glucose-loaded rats in experiment 2. Each point represents the mean ± S.E.
Legend: -○-; Glucose levels of control rats receiving no herb mix, -△-; Glucose levels of rats treated with herb mix, -●-;, -▲-;, *: p<0.05, **: p<0.01.

MEDICINAL COMPOSITION FOR DIABETES

TECHNICAL FIELD OF THE INVENTION

The present invention relates to a composition for treating diabetes, a method for making the composition, and a kit containing active ingredients suitable for treating diabetes.

BACKGROUND OF THE INVENTION

Diabetes afflicts a significant number of people, approximately 5 %, and yet the treatment of diabetes leaves a lot to be desired. For patients with Type I diabetes, insulin is an absolute necessity. It is typically administered by injection, needs to be coordinated with a balanced diet and exercise, and must be carefully monitored. For subjects with Type II diabetes (over 90% of all cases of diabetes), weight loss is advisable, but is frequently usually difficult to achieve; tablets, such as oral hypoglycemic agents, or insulin may be required. Despite all this effort diabetes complications—blindness, kidney failure, nerve damage, and atherosclerosis—still exact an enormous toll.

The only new class of medications to appear in the treatment of diabetes in the last 40 years have been α-glucosidase inhibitors. These have a modest effect on postprandial glucose levels, but have gastrointestinal disturbance and flatulence as side effects. Other agents such as free fatty acid inhibitors are still being tested.

SUMMARY OF THE INVENTION

The present invention relates to a medicinal composition for the treatment of diabetes, and a method for making the composition. It has been found that compositions containing extracts derived from *Heracleum lanatum* plant material and plant material extracts derived from a species of Populus exhibit medicinal benefits in the treatment of diabetes. *Heracleum lanatum* is a herb also known as cow parsnip, from the Umbrelliae family. The genus Populus is in the Salicaceae (willow) family, and includes many tree species and shrub species found throughout the world, mostly in north temperate or arctic regions. A preferred species, *Populus tremuloides*, is also known as a quaking aspen, a trembling aspen, or a golden aspen.

There are many types of teas made from natural substances, such as Ginko, Persimmon, and Pine. However, it is unknown to provide a medicinal composition made from plant material derived from *Heracleum tantalum* and a species of Populus. This combination is not listed in detailed herbal medicine compendiums or in American native herbal remedy compendiums. In addition, *Heracleum lanatum* is not listed as an herbal remedy, although bark form Populus species has been suggested for treating an upset stomach. Thus, the antidiabetic effects of this combination are quite unexpected.

BRIEF DESCRIPTION OF THE DRAWINGS

FIG. 1 shows the results of a first experiment demonstrating the effects of herb mix extract on plasma glucose and FFA (free fatty acid) concentration in glucose-loaded rats.

FIG. 2 shows the results of a second experiment demonstrating the effects of herb mix extract on plasma glucose and FFA (free fatty acid) concentration in glucose-loaded rats.

DETAILED DESCRIPTION OF THE INVENTION

The present invention relates to a method for treating diabetes involving administering a tea having extracts derived from *Heracleum lanatum* and a species of Populus. In a preferred embodiment of the invention, the Populus species is *Populus tremuloides*.

The present invention also relates to a composition including extracts from *Heracleum tantalum* cells and cells from a species of Populus, preferably *Populus tremuloides*.

The present invention also relates to a method for producing a diabetes medicant comprising mixing plant material from *Heracleum lanatum* and plant material from a species of Populus in a solution, preferably a heated solution such as a tea.

The present invention also includes a kit having dried materials derived from *Heracleum lanatum* and from a species of Populus, and may also include at least one of the following: a strainer or the like, a measuring device for measuring the amount of herb extract, a measuring device for measuring the amount of water, and a cup or container for brewing and or drinking the tea.

As used herein, dry matter is a term of art typically referring to the material remaining after harvesting fresh plants or plant parts, and heating the harvested material until all the water is removed. Principal components of dry material typically include, but are not limited to, cell membrane polysaccharides and lignin, and protoplasmic components, such as proteins, lipids, amino acids, organic acids, and certain elements that exist as ions but form no essential part of an organic compound (e.g., potassium, among others).

As used herein, material derived from *Heracleum lanatum* refers to plant material derived from any part of the plant at any stage of its growth. Exemplary material includes but is not limited to parts of the plant, such as seeds, bark, roots, shoots, flowers, and leaves; plant-derived proteins; plant-derived carbohydrates; and parts, portions, or extracts of any of the above. In a preferred embodiment of the invention, the material is dry matter derived from the seed tops and stems of the *Heracleum lanatum* plant, or extracts derived from the seeds and/or stems. In a most preferred embodiment of the invention, the dry matter is derived from mature tops or seed pods.

As used herein, material derived from a species of the genus Populus refers to material derived from any part of the tree at any stage of its growth, as defined above. Exemplary species of the genus Populus includes but is not limited to *Populus acuminata, Populus alba, Populus angustifolia, Populus balsamifera, Populus deltoids, Populus grandidentata, Populus heterophylla, Populus nigra, Populus sargentii, Populus tremuloides* and *Populus tricocarpa*.

In a preferred embodiment of the invention, the material is dry matter, as defined above, derived from leaves or extracts of the leaves, preferably from young trees (less than about 15 years old). In a most preferred embodiment of the invention, the dry matter is derived from leaves of *Populus tremuloides*.

In accordance with the present invention, it will be appreciated that the composition may be provided in several forms, including but not limited to a tea bag, loose dry matter, in a tablet, or capsulized. For example, if it desirable to formulate the composition into a tea, the composition may be in the form of loose dry material or may be collected in a filter bag, such as a tea bag. If it is desirable to formulate the composition into an extract, the composition may be in the form of solid, a somewhat viscous liquid, a syrup, a tonic, a concentrated liquid, or as a canned beverage. The composition may be in hot or cold form. In an embodiment of the invention, an aqueous extract may be formed by concentrating the active ingredients or dry material in a liquid, and evaporating the liquid content to form an extract formulation.

In accordance with the present invention, the medicinal composition may be administered by any means suitable for delivering an effective dose of the active ingredient(s) of the composition. Exemplary mechanisms for administering the composition include, but are not limited to drinking or ingesting a solution, such as a tea; a crushed or ground mixture of the dry material, such as a powder or granules, placed in a capsule, or pelletized into a tablet, or the like; a crushed or ground mixture of the dry material as a powder, directly ingested orally or thinally, drinking or ingesting a solid or liquid extract of the plant material; and drinking or ingesting a solid or liquid extract of the plant material that has been reconstituted into a tea or beverage or the like.

In accordance with the present invention, the herbal remedy may be produced by brewing dry matter as defined above, in water for a time sufficient to produce a "tea". Typically, the brewing can be accomplished in 20 minutes or so, but the invention is not to be limited by the amount of brewing time.

In accordance with the present invention, the herbal remedy may also be produced by extracting the active ingredients in an organic solvent or the like. For example, dry matter, such as leaves, may be crushed and then soaked in an organic solvent, including but not limited to ether, ethanol, chloroform, hexane, acetone, and the like. The solvent is then removed from the extract, leaving an active component that can be placed in a tablet, capsule, tonic, or other form as described above.

A composition according to the invention may also include one or more of a number of other ingredients. Exemplary additional ingredients include, but are not limited to vitamins, such as vitamins A, C, and K; coloring agents; minerals; sweeteners, such as glucose or fructose, or artificial sweeteners; or flavoring agents, including, but not limited to mint, jasmine, berry extracts, citrus extracts, and other natural or artificial flavorings.

In accordance with the invention, the composition may be administered at any rate, dosage, or over any time period found effective for the treatment of diabetes. For example, it has been found effective to administer the composition by drinking a cup of the tea over four consecutive days during the first week and then again for four days the following week.

In accordance with the invention, the medicinal composition may be prepared by a process which involves providing a predetermined quantity of *Heracleum lanatum* plant material, preferably dry material derived from seed tops and stems; providing a predetermined quantity of a species of Populus plant material, preferably dry material derived from leaves, most preferably leaves from the *Populus tremuloides* species; and mixing the plant material.

Optionally, it may be desirable to then soak the mixture for a predetermined period, e.g., two to four hours, at about 10° C. to about 20° C., to remove or reduce any bad smell or bad taste, such as that sometimes caused by the presence of tannin. It may also be desirable to conduct this step under pressure, e.g., in a pressure pot.

The mixture, with or without the above optional step, may then be soaked for a predetermined period, e.g., typically two to four hours, after which the mixture may be heated from about 5 minutes to about several hours at a temperature of up to about 130° C. In an alternative embodiment of this step, the mixture may be exposed to steam for a predetermined period in order to produce a tea or an extract.

One skilled in the art will recognize that varying the conditions of the processing, e.g., the amount of heat, time, or pressure, will affect the product. For example, heating the mixture for a longer period may result in a solid or semi-solid extract of the mixture; heating the mixture for a short period may result in an ingestible tea.

EXAMPLES

Example 1

The herbal remedy is made by taking two herbs and brewing them in water for one to two hours to generate a "tea". The patients were given the tea for four consecutive days during the first week and then again for four days the following week.

In the first phase of the study nine patients were entered. Some were given the herbal tea and the remainder a blend of commercial teas generated to act as a placebo. The patients were not told which tea they were being given. After full diet history was taken, the patients were asked to monitor their blood glucose four times a day for a week prior to entering the study, to maintain their usual diet, activity and diabetes medications. They then attended and were given their tea for four days. If low blood glucose values occurred, their diabetes medication dosage was reduced. The following week they had another four days of tea and then were followed over the next two and four weeks. Diet was again recorded, together with weight, diabetes medications, and general well being. Any adverse events were noted. The Results are provided in the tables. Table 1 is the data for those receiving the tea, and Table 2 for those on the placebo.

In the Tables, ⇓ represents a decrease; ↑, an increase; →, to; GI, gastrointestine; DM, diabetes mellitus; post brk, after breakfast; URTI, upper respiratory tract infection; and 4 U, four units.

Summary

Four of the five patients receiving the tea had an improvement in their glucose control as evidenced by maintaining a lower blood glucose level, a reduced dose of medication, or both, as compared to before receiving the herbal remedy. The fifth patient had reduced his insulin by more than a third masking any possible improvement in glucose control. Four of the five patients also had a reduction in their diabetes medication dosages. None of the patients receiving the placebo had a reduction in their diabetes medications though two of the four had an improvement of their glucose control. On follow-up four weeks later three of the five subjects given the herbal tea maintained the improvement but only one of the control subjects had still improved glucose control.

TABLE 1

Evaluation at end of study A for subjects receiving herbal tea

| Subject | Type of DM | Wt. Change | Diet Change | Well-being | Medications | Glucose | Outcome Four weeks later |
|---------|------------|------------|-------------|------------|-------------|---------|--------------------------|
| 3A, ♀ Age 61 | II | ↑ 1.4 kg | Slight ⇓ in snacks | Better | Glyburide ⇓, 20 to 10 mg Metformin ⇓, 1500 to 10000 mg | Fasting 8.7 → 8.3 mM Post Brk 6.8 → 5.5 mM Postlunch 6.5 → 4.9 mM | At 2 weeks weight decreased minimally and glucose remains improved |
| 4A, ♀ Age 54 | II | ⇓ 0.8 kg | Same | Same | Glicazide ⇓, 80 to 0 mg | Fasting 9.8 → 6.9 mM Prelunch 8.9 → 7.1 mM Presupper 8.7 → 6.6 mM | Glucose improved |
| 8A, ♀ Age 67 | II | ⇓ 2.5 kg | Slight ⇓, GI upset | GI upset, abd. pain, nausea, diarrhea | Just on diet | Fasting 7.5 → 7.0 mM Prelunch 6.0 → 5.2 mM Presupper 8.9 → 10.3 mM PreBedtime 6.2 → 5.9 mM | Weight decreased and glucose the same |
| 6A, ♂ Age 53 | II | ⇓ 0.5 kg | Minimal ⇓ in snacks | Better | Insulin ⇓, 30 to 18 Units | Fasting 8.3 → 7.4 mM Prelunch 10.9 → 9.2 mM Presupper 11.2 → 7.2 mM PreBedtime 14.0 → 8.6 mM | Weight maintained, glucose and insulin back to baseline |
| 9, ♂ Age 30 | I | ⇓ 3.0 kg | Some ⇓ but also ⇓ exercise | Better | Insulin ⇓, 53 to 33 Units | Fasting 8.9 → 11.6 mM Prelunch 8.4 → 8.9 mM Presupper 8.8 → 13.9 mM PreBedtime 11.2 → 14.4 mM | Some weight regained, insulin and glucose returned to baseline |
| Summary | | 3/5 lost some weight | 3/5 slight ⇓ | 3/5 Better, 1/5 GI upset | 4/5 ⇓ medication dose | 4/5 improved glucose control and fifth patient had higher glucose levels but taking 62% of baseline insulin | 3/5 held improvement |

TABLE 2

Evaluation at end of study A for subjects not receiving herbal tea

| Subject | Type of DM | Wt. Change | Diet Change | Well-being | Medications | Glucose | Outcome Four weeks later |
|---------|------------|------------|-------------|------------|-------------|---------|--------------------------|
| 1A, ♂ Age 67 | II | ↑ 0.4 kg | Same | Better | Same | Fasting 5.8 → 5.5 mM Postlunch 10.8 → 9.6 mM PreBedtime 10.1 → 10.6 mM | Glucose slightly higher, but Metformin ↑ |
| 2A, ♂ Age 46 | II | ⇓ 0.9 kg | Slight ⇓ in snacks | Worse | Same | Fasting 10.0 → 9.8 mM PreBedtime 11.0 → 10.1 mM | Glucose slightly better but Glyburide ↑ |
| 5A, ♀ Age 52 | II | ⇓ 1.5 kg | Minimal ⇓ | Same | Same | Fasting 9.2 → 8.2 mM Prelunch 14.1 → 8.2 mM Presupper 12.2 → 11.0 mM PreBedtime 12.7 → 8.7 mM | Glicazide increased and glucose back to baseline |
| 7, ♂ Age 35 | II | ↑ 1.0 kg | ⇓ Intake | Same | Glicazide unchanged | Fasting 13.7 → 10.2 mM Prelunch 14.5 → 11.6 mM Presupper 16.5 → 10.8 mM PreBedtime 16.8 → 13.0 mM | At two weeks further weight loss and glucose remains improved |
| Summary | | 3/4 ⇓ weight | 3/4 ⇓ | 1/4 better 1/4 worse | No change | 2/4 improved | 1/4 Improved |

Example 2

Following the encouraging results of the first study, and to reduce the possibility that the first test results were inaccurate due to the possibility that the patients developed some idea if they were on the herbal tea or the placebo, a second study was planned. During this study, the patients had minimal contact with each other and were prevented from knowing which tea they were receiving. Eleven patients were recruited for this study. The placebo again was a blend of commercially available teas. The subjects attended an information session and then for four days received either the placebo tea or the herbal tea. The following week they received a supply of tea for a further four days. Prior to the study they monitored their glucose four times a day for a week and continued this during and for four weeks after the study. General well being, diabetes medications and as a measure of the average blood sugar, the HbAlc was assessed. The results are shown in the following two tables, 3 and 4, for those receiving the herbal tea and placebo respectively.

Summary

At the end of the study period four of seven patients receiving the herbal tea had improved glucose levels and 4 had reduced their diabetes medications and none increased their diabetes medications. The measure of the average blood glucose the HbAlc was also improved in four. In the placebo treated group three of five showed some improvement and three also decreased their diabetes medications but one had to increase his medication. On follow-up five of seven patients given the tea had improved glycemic status but only one of the five patients given placebo had continued improvement. Thus although the results in this phase are less striking during the period that the subjects ingested the tea, the continued improvement is dramatic and warrants further study.

TABLE 3

Evaluation at end of the second study for subjects receiving herbal tea

| Subject | Type of DM | Wt. Change | Diet Change | Well-being | Medications | Glucose | % HbA1c Pre | % HbA1c Post | Outcome Four weeks later |
|---|---|---|---|---|---|---|---|---|---|
| 2B, ♂ Age 44 | II | ⇓ 2.4 kg | Slight ⇓ | Same | Metformin ⇓, 1500 to 1000 mg | Fasting 7.1 → 6.0 mM PostBrk 6.5 → 7.3 mM Postlunch 6.5 → 5.8 mM PreBedtime 6.1 → 7.3 mM | 6.2 | 6.1 | Medication decreased further but glucose slightly ⇑ due to URTI |
| 9B, ♂ Age | II | ↑ 4.2 kg | Same | Same | Same dose of insulin | Fasting 6.6 → 8.7 mM Prelunch 7.0 → 9.3 mM Presupper 7.5 → 13.1 mM PreBedtime 5.9 → 6.8 mM | N/A | N/A | N/A |
| 10B, ♂ Age 58 | II | ↑ 1.0 kg | Same | Same | Insulin ⇓, 29 to 18 Units | Fasting 8.1 → 8.7 mM Prelunch 8.4 → 7.8 mM Presupper 8.0 → 6.4 mM | 7.5 | 7.8 | Insulin back to baseline glucose better |
| 11B, ♀ Age 45 | II | ⇓ 0.3 kg | Same | Worse | Same on no medication | Fasting 10.0 → 9.8 mM PostBrk 9.4 → 10.6 mM | 8.3 | 8.5 | Unchanged |
| 3B, ♂ Age 18 | I | ↑ 1.9 kg | Same | Same, had URTI during tea period | Same dose of insulin | Fasting 10.5 → 11.2 mM Prelunch 9.3 → 9.3 mM Presupper 13.8 → 8.4 mM PreBedtime 8.9 → 6.5 mM | 9.4 | 8.9 | Glucose much better |
| 4B, ♀ Age 44 | I | ↑ 2.5 kg | Same | Better | Insulin ⇓, 34 to 32 Units | Fasting 9.7 → 7.1 mM Prelunch 8.6 → 7.4 mM Presupper 11.1 → 9.1 mM PreBedtime 8.7 → 9.1 mM | 8.8 | 7.6 | Glucose further improved on same lower dose of insulin |
| 8B, ♀ Age 37 | I | ⇓ 0.5 kg | Same | Same | Insulin ⇓, 53 to 46 Units | Fasting 7.7 → 8.8 mM Prelunch 7.2 → 11.9 mM Presupper 8.3 → 5.9 mM PreBedtime 8.1 → 13.7 mM | 8.4 | 8.3 | Glucose further improved and insulin returned to 4U above baseline |
| Summary | | 4/7 ↑ and 3/7 ⇓ | 7/7 Same | 1/7 Worse and 1/7 Better | 4/7 Decreased medication dose | 4/7 Better and 1/7 Worse | 4 better, 2 worse | | 5/7 Better |

TABLE 4

Evaluation at end of second study for subjects not receiving herbal tea

| Subject | Type of DM | Wt. Change | Diet Change | Well-being | Medications | Glucose | % HbA1c Pre | % HbA1c Post | Outcome Four weeks later |
|---|---|---|---|---|---|---|---|---|---|
| 5B, ♂ Age 60 | II | ↑ 0.5 kg | Same | Slightly Better | Glyburide unchanged Metformin ⇓, 1500 to 1000 mg | Fasting 7.7 → 6.9 mM Postlunch 11.4 → 9.6 mM PreSupper 13.6 → 11.6 mM | 10.1 | 9.4 | Glucose returned to baseline |
| 6B, ♂ Age 61 | II | ↑ 0.7 kg | Same | Slightly Worse | Glyburide unchanged Metformin added | Fasting 9.3 → 9.9 mM PostBrk 11.2 → 13.0 PostLunch 11.1 → 14.8 mM PostSupper 12.7 → 12.5 mM | N/A | N/A | Glucose slightly better but on Metformin as new therapy |
| 7B, ♂ Age 48 | II | ↑ 1.2 kg | Same | Same | Insulin dose unchanged, 130 Units | Fasting 7.9 → 7.3 mM Presupper 12.0 → 7.9 mM PreBedtime 11.4 → 10.8 mM | 7.9 | 7.7 | Glucose slightly better but increased exercise |
| 12B, ♂ Age 33 | I | ↑ 0.5 kg | Same | Same | Insulin ⇓, 68 to 63 Units | Fasting 7.8 → 8.3 mM Prelunch 9.0 → 6.7 mM PreSupper 10.2 → 5.1 mM PreBedtime 8.1 → 8.8 mM | N/A | N/A | Insulin dose back up 3 units and glucose remains better |
| 1B, ♀ Age 20 | I | Same | Slight ⇓ | Same | Insulin ⇓, 30 to 26 Units | Fasting 5.0 → 5.8 mM Prelunch 7.4 → 4.5 mM PreSupper 5.6 → 9.8 mM PreBedtime 11.6 → 9.4 mM | 8.3 | 8.5 | Glucose worse and insulin dose back to baseline |
| Summary | | 4/7 Slight ↑ | 1/5 Slight ⇓ | 3/5 Same | 3/5 slightly lower med. dose and 1/5 increased dose | 3/5 Better and 1/5 Worse | 2 better, 1 | | 1/5 better and 2/5 worse |

Example 3
Preparation of herbal antidiabetic extract

1. The two components used are the dried seed-tops and stems of *Heracleum lanatum* and the dried leaves of *Populus tremuloides*.

2. The two dried components are mixed in a ration of 1:1 although we believe that mixtures between 3:1 and 1:3 would also be effective.

3. To prepare the extract, a minimum of 10 grams of the 1:1 herbal mixture is boiled for approximately 20 minutes in approximately 1 liter of water. The resulting tea is consumed as a treatment for both non-insulin dependent diabetes and insulin-dependent diabetes (although in the latter case the need for insulin is reduced, not eliminated). Although 10 grams is listed as a minimum amount, 20 grams is commonly used and was used for clinical studies. The use of amounts greater than 20 grams only result in a more potent extract.

4. Dosage schedules vary. We have found that a single daily consumption of 4–8 ounces of the tea for two four-day periods (separated by four days) is effective at improving diabetes control for at least one month (as demonstrated in the studies) and, anecdotally, for up to 6 months. We have also found that administering 4–8 ounces of the tea on a daily basis for two weeks in also effective. This also results in improved diabetic control for one to six months. Daily consumption, we believe, might prove too potent at the doses used, but might be acceptable if lower doses were chosen.

5. Notwithstanding the dosages and dosage schedules listed above, the end clinical effect is a combination of both duration and extract potency such that as potency increases, duration can decrease and vice versa.

Example 4
Preparation of an herbal mixture

In the first experiment, 9.8 grams of the herbal mixture was extracted for 20 minutes in 500 ml of boiling water. The solution was filtered, concentrated to ⅓, and freeze-dried to obtain 2.14 grams of solid extract. This solid extract (1 gram per kilogram body weight) along with glucose (1.5 grams per kilogram body weight) was given simultaneously by stomach tube to seven week old male Wistar rats after 17 hours of fasting. Blood was taken from the tail vein and glucose and free fatty acid (FFA) concentration was measured enzymatically. Results of this study show that the herbal mixture decreased the peak glucose concentration but extended the rise in glucose at later time points compared to the control (FIG. 1). These properties are desirable in an anti-diabetic medication as theoretically high post-prandial glucose level would be avoided and a more sustained blood sugar in response to meals would be obtained. Thus, in the latter case, there would be less chance for rebound hypoglycemia.

In a second identical experiment, identical results were achieved using a different lot number of the herbal extract (FIG. 2). Thus, the effect of the herbal mixture is consistent and repeatable.

The effect of the extract obtained in Example 4 was tested on various enzymes. In these studies, the breakdown of the specific substrate was tested in the presence of the herbal mixture, of substances known to specifically inhibit the respective enzyme or in the presence of controlled powder. The concentrations of herb necessary to inhibit 50% of the enzyme activity are given in the middle column of Table 5. This data shows that there is some significant inhibition of aldose reductase activity by the herb mixture. This finding shows that aldose reductase may be partially responsible for certain diabetic complications such as neuropathy. It also shows that the herbal extract's mechanism of action may be different from that of acarbose, which is the newest antidiabetic product being commercially developed.

TABLE 5

Inhibitory effects of canadian herb mix extract on aldose reductase, maltase, sucrase, α-amylase, α-glucosidase, prolyl endopeptidase and tyrosinase

| Enzyme | Inhibitory activity ($IC^{50}$:μg/ml) | |
| --- | --- | --- |
| Aldose reductase (rat lens) | 7.0 | 0.015 (sorbinil) |
| Maltase (rat small intestine) | >300 | 3.5 (acarbose) |
| Sucrase (rat small intestine) | >300 | 4.2 (acarbose) |
| α-Amylase (porcine pancreas) | >100 | 0.62 (acarbose) |
| α-Glucosidase (yeast) | >100 | 350 (acarbose) |
| Prolyl endopeptidase (flabobacterium sp.) | >100 | 0.009 (Z-Pro-prolinal) |
| Tyrosinase (mushroom) | >300 | 4.3 (kojic acid) |

Example 5
In vitro toxicity tests.

A third series of tests looked at in vitro toxicity. The results illustrated in Table 6 indicate that the herb extract did not have significant dose-dependent toxicity on these cells confirming its relative safety for human consumption.

TABLE 6

Cytotoxity in KB cells by canadian herb mix extract

| Canadian herb mix extract (μg/ml) | Inhibition % |
| --- | --- |
| 3 | −7.22 |
| 10 | −7.96 |
| 30 | −13.02 |
| 100 | −20.87 |
| 300 | −8.4 |

Although the present invention has been described in terms of a particular preferred embodiments, it is not limited to those embodiments. Alternative embodiments, examples, and modifications which would still be encompassed by the invention may be made by those skilled in the art, particularly in light of the foregoing teachings. Therefore, the following claims are intended to cover any alternative embodiments, examples, modifications, or equivalents which may be included within the spirit and scope of the invention as defined by the claims.

I claim:

1. A composition comprising plant material derived from *Heracleum lanatum* and plant material derived from a Populus species wherein ratio of *Heracleum lanatum* to Populus species is from about 3:1 to about 1:3.

2. The composition of claim 1 wherein the Populus species is *Populus tremuloides*.

3. The composition of claim 1 wherein the *Heracleum lanatum* comprises seed-tops and stems.

4. The composition of claim 1 wherein the Populus species comprises leaves.

5. The composition of claim 1 wherein the ratio is 1:1.

6. The composition of claim 1 wherein the composition is in the form of a solution, a syrup, a tonic, dry matter, powder, or granules.

7. A method for treating diabetes comprising administering to a patient in need thereof an effective amount of a composition comprising plant material derived from *Heracleum lanatum* and plant material derived from a Populus species.

8. The method of claim 1 wherein administering an effective amount of a Populus species comprises administering *Populus tremuloides*.

9. The method of claim 1 wherein administering an effective amount comprises administering a solution containing an effective amount of plant material derived from *Heracleum lanatum* and plant material derived from a Populus species wherein ratio of *Heracleum lanatum* to Populus species is from about 3:1 to about 1:3.

10. The method of claim 9 wherein administering a solution comprises administering a heated solution.

11. The method of claim 9 wherein administering a solution comprises administering a cool or cold solution.

12. A method of producing a diabetes medicant comprising mixing in a solution a predetermined amount of *Heracleum lanatum* and a predetermined amount of a Populus species wherein ratio of *Heracleum lanatum* to Populus species is from about 3:1 to about 1:3, and heating the solution.

13. A method of controlling the in vivo amount of glucose comprising administering to a patient in need thereof an effective amount of a composition comprising plant material derived from *Heracleum lanatum* and plant material derived from a Populus species.

14. The method of claim 13 wherein the composition is in the form of a solution, a syrup, a tonic, dry matter, powder, granules, or a tablet or capsule containing dry matter, powder, or granules.

15. The method of claim 13 wherein controlling the in vivo amount of glucose further comprises inhibiting an enzyme selected from the group consisting of aldose reductase, maltase, sucrase, α-amylase, α-glucosidase, propyl endopeptidase, and tyrosinase.

16. A method for treating diabetes comprising:
   boiling a plant material mixture comprising the dried seed-tops and stems of *Heracleum lanatum* and the dried leaves of a Populus species in a ratio of from about 3:1 to about 1:3 in water to form a tea wherein the proportion of said plant material to water is about 1% w/w or greater, and
   administering to a patient in need thereof an effective amount of said tea.

17. The method of claim 16 wherein said tea is administered at a dosage of about 4 to 8 ounces of said tea per day for a first four day interval and for a second four day interval wherein said first interval is separated from said second interval by four days.

18. A kit to be used for the treatment of diabetes comprising;
   dried material derived from *Heracleum lanatum* and a Populus species,
   a means for separating said materials from water, and
   a measuring device for measuring the amount of said dried material or water.

19. A product to be used for the treatment of diabetes comprising;
   dried material derived from *Heracleum lanatum* and a Populus species, and
   a filter bag.

* * * * *